United States Patent
Roshkovan

(10) Patent No.: US 11,510,754 B2
(45) Date of Patent: Nov. 29, 2022

(54) SURGICAL DRILL GUIDE AIMED AT LOCATING IDEAL POSITION FOR DENTAL IMPLANTS IN EDENTULOUS PATIENTS

(71) Applicant: Igor Roshkovan, Los Angeles, CA (US)

(72) Inventor: Igor Roshkovan, Los Angeles, CA (US)

( * ) Notice: Subject to any disclaimer, the term of this patent is extended or adjusted under 35 U.S.C. 154(b) by 530 days.

(21) Appl. No.: 16/350,996

(22) Filed: Feb. 11, 2019

(65) Prior Publication Data
US 2020/0253690 A1    Aug. 13, 2020

(51) Int. Cl.
| | | |
|---|---|---|
| *A61C 1/08* | (2006.01) | |
| *A61C 8/00* | (2006.01) | |
| *A61B 17/17* | (2006.01) | |

(52) U.S. Cl.
CPC ............ *A61C 1/084* (2013.01); *A61C 8/0089* (2013.01); *A61B 17/17* (2013.01)

(58) Field of Classification Search
CPC ....... A61C 1/084; A61C 8/0089; A61C 1/082; A61B 17/17; A61B 17/176
See application file for complete search history.

(56) References Cited

U.S. PATENT DOCUMENTS

| | | | | |
|---|---|---|---|---|
| 2005/0037320 A1* | 2/2005 | Poirier | ................... | A61C 1/084 433/173 |
| 2014/0272778 A1* | 9/2014 | Llop | ................... | A61C 8/0089 433/72 |
| 2014/0272780 A1* | 9/2014 | Llop | ................... | A61C 8/0048 433/75 |
| 2015/0037756 A1* | 2/2015 | Berckmans, III | .... | A61C 9/0006 433/173 |
| 2016/0278878 A1* | 9/2016 | Watson | ................... | A61B 17/17 |

FOREIGN PATENT DOCUMENTS

| | | | | |
|---|---|---|---|---|
| EP | 0534552 A1 * | 3/1993 | ........... | A61C 8/0027 |
| EP | 0534552 A1 | 3/1993 | | |
| EP | 2060240 A2 * | 5/2009 | ............ | A61C 1/084 |
| EP | 2377486 A1 * | 10/2011 | ............ | A61C 1/084 |
| EP | 2377486 A1 | 10/2011 | | |
| EP | 2465462 A2 | 6/2012 | | |
| EP | 3569185 A1 * | 11/2019 | ............... | A61C 8/00 |
| WO | 2004064664 A1 | 8/2004 | | |
| WO | 2017069797 A1 | 4/2017 | | |

OTHER PUBLICATIONS

European Patent Office, European Search Report for application 20000112.1, dated Jun. 20, 2020.

\* cited by examiner

*Primary Examiner* — Amy R Weisberg

(57) ABSTRACT

This document describes a set of surgical drill guides for the upper and lower jaw, the guides aimed at locating the ideal position for dental implants in edentulous patients. The guides are made up of a surgical stent material from metal or other rigid material that is aligned to provide support and stability of fully edentulous upper and lower jaw to orient surgical drills in the area of operation. The present embodiment comprises a U-shape metal plate provided form or shaped resembling a toothless upper or lower jaw and containing a top surface of the surgical stent that is contacting the soft tissue of maxilla or mandibula and the bottom surface of the stent that has the same shape as a top one.

6 Claims, 14 Drawing Sheets

US 11,510,754 B2

SURGICAL DRILL GUIDE AIMED AT LOCATING IDEAL POSITION FOR DENTAL IMPLANTS IN EDENTULOUS PATIENTS

BACKGROUND—PRIOR ART

This embodiment is in field of dental prostheses and methods and apparatus for performing dental fixed implant retained bridges, removable overdentures or screw retained overdentures and for set up dental intraoral prostheses in the mouth of patients.

This disclosure concerns improved dental care for edentulous patients, toothless patients or patients lacking teeth. The inventions include a novel surgical guide aimed at locating ideal position for dental implants in edentulous patients. This embodiment relates particularly to surgical drill guide device aimed at locating ideal position for dental implants in patients without teeth and providing an improved surgical guide for installing and insertion of dental implants. This embodiment has a reference to the portion of dental device, methods and apparatus as a surgical guide aimed at locating the ideal position for dental implants in edentulous patients that is particularly adapted for dental use, which allows for more efficient function of the placement of dental implants in edentulous patients.

The following is a tabulation of teachings that may relate to the invention described herein:

| Pat. No. | Kind Code | Issue Date | Patentee |
|---|---|---|---|
| U.S. Patents | | | |
| 9,211,165 | B2 | 2015 Dec. 15 | Jamison |
| 8,105,081 | B2 | 2012 Jan. 31 | Bavar |
| 7,097,451 | B2 | 2006 Aug. 29 | Tang |
| 5,967,777 | A | 1999 Oct. 19 | Klein et al. |
| 5,320,529 | A | 1994 Jun. 14 | Pompa |
| 5,133,660 | A | 1992 Jul. 28 | Fenick |
| U.S. Patent Application Publications | | | |
| 20090130630 | A1 | 2009 May 21 | Zachary et al. |

Modern implant dentistry usually involves restoring teeth in an edentulous patient by using dental implants to reconstruct intraoral defects with the help of dental prosthesis.

Dental prosthesis means a set of artificial teeth that is designed to reestablish esthetically and functionally missing teeth in edentulous patients.

Dental implants surgical drill guide means a fitting device that is used by a dentist to establish the right position for drilled apertures for the insertion of dental implants.

The present embodiment relates generally to a surgical drill guide aimed at locating ideal position for dental implants in edentulous patients and to techniques, methods and apparatus for locating the ideal placement of dental implants when patient doesn't have any teeth at all. In this situation it is very difficult to locate the right position for the insertion of dental implants.

The positioning guides may also be called dental implant placement guides for edentulous patients, implant dental drill guides for edentulous patients, or surgical drill guides aimed at locating the ideal position for dental implants in edentulous patients In the majority of cases, the prosthetic device is indistinguishable from a natural tooth. In this way, patients who are edentulous because they have lost the all of their teeth structures can obtain several prosthetic replacements. It is not currently possible to insert dental implant in a precise anatomical position.

This inability to achieve a correct anatomical orientation can occur for a number of reasons. Most obviously, the patient's lack of any natural teeth prevents appropriated orientation. Unquestionably, the dental implants must align in the same angulation as the natural teeth. The dental practitioner may choose the position to place the implant in the jaw at an angle to a precise vertical direction but it's very difficult when patient doesn't have natural teeth. Volume and quality of bone tissue of jaw are critical elements for deliberate anatomical positioning and for the proper angularity in the insertion process of the dental implants, particularly for edentulous patients.

The dental implant surgery initially involves making an incision in the gum tissue to uncover the underlying bone. After that, an initial hole is drilled in the initial layer of bone to establish the position and the initial depth for the future dental implant. The diameter of first hole is generally smaller in diameter than the diameter of dental implant and will be enlarged during the surgical procedure using standard drilling protocol for the dental implant insertion.

The dental provider during the dental implant surgery uses a parallel technique or positioning guide technique to establish the parallel and right angulations of the initial holes drilled into the bone and extending outwardly from bone.

The dentist can detect the orientation of the extending portion of the parallelism and analyses of the future position of the dental implants. In case of edentulous, the patient's dental surgeon has no reference points and very difficult task to drill the initial holes to create the appropriate spacing between adjacent holes and to established parallel positioning.

As a result, there is a need for a surgical drill guide which effectively helps aim at the right position for the dental implants for toothless patients. It is usually important that the dental implant be inserted at the proper approach with respect to the individual structure of the alveolar bone of the patient.

In implant dentistry we are exceptionally limited in methods and devices that have been developed for the correct placement of a dental implant in edentulous patients. Some techniques depend only on the skill and experience of the dental provider for positioning and installing the implant in these cases.

BRIEF SUMMARY AND OBJECT OF THE EMBODIMENT

In reaction to the complications and problems discussed herein, a very effective surgical drill guide aimed at locating ideal position for dental implants in edentulous patients is provided.

One embodiment of the present disclosure is directed to a surgical drill guide aimed at locating the ideal position for dental implants in edentulous patients, comprising a surgical stent material from metal or other material from which the surgical guides are made. The guides must have the features of being relatively rigid so that the guide is aligned to provide support and stability of fully edentulous upper and lower jaw to navigate orientation surgical drills in area of operation.

The casting apparatus is formed or shaped resembling a toothless upper or lower jaw which can be positioned to dental area to be restored.

The present invention relates to an improved mounting device and apparatus for use in the area of surgery with studs comprising slot channels that imitate the position of natural teeth.

Therefore, an item of present embodiment is to provide a new concept and value-added surgical guide aimed at navigating the ideal position for dental implants in edentulous patients during dental procedures.

An advance object of the current invention is to provide a way that can enhance the function of a surgical guide.

An item of present current invention consists of two plates joined together by several screws.

The present embodiment comprises a metal plate containing a top surface of the surgical stent that has a shape reminiscent of the shape of the upper or lower jaw that contacts the soft tissue of maxilla and mandibula and the bottom surface of the stent has the same shape as the top one.

In another embodiment, the surgical guide stent for lower jaw has a U-shape cross section and is comprised of metal material. Moreover the surgical drill guide for upper jaw is generally fan-shaped in design whereas the surgical guide for lower jaw is U-shaped and corresponds to the forms and contour of upper and lower jaws of the patient. The internal surface of present invention is anatomically contoured to match respectively over either of the upper and lower jaw and contacting soft tissue.

The base of the surgical guide is aimed at locating the ideal position for dental implants in edentulous patients. It is formed of metal or any other rigid material which allows the base to adapt to the anatomical structure of individual patient mouth and proved a relatively tight seal between base and adjacent soft tissue.

In this manner the surgical guide is retained securely against any movement and provides a very accurate navigation for the subsequent drilling protocol.

The present embodiment comprises a metal plate containing one major slot channel along the axis of the surgical guide stent with fourteen mounting points in the position of the fourteen teeth on upper or lower jaw.

In other embodiment, the major perforated L track make up a supplemental short slot channels with extended positions corresponding to the natural position of absent teeth. The major perforated L track extends to the buccal and lingual sides allowing the positioning of all fourteen teeth in upper or lower jaws by extending major L track.

The present invention is also directed to a mounting apparatus for use with a stud slot channel.

The surgical guide may accommodate employment of two or more mounting devices on major perforated L track with distance of 3-4 mm there between.

The foregoing advantages and objectives of the present embodiment will be more gladly understood upon consideration of the following detailed description of the present invention taken in combination with the selected drawings.

BRIEF DESCRIPTION OF THE DRAWINGS

With the above and supplementary items and advantages in view, as will hereinafter appear, this present embodiment comprises the devices, described by way of example and illustrated in the following drawings.

DRAWING-REFERENCE NUMERALS

Figure 1:
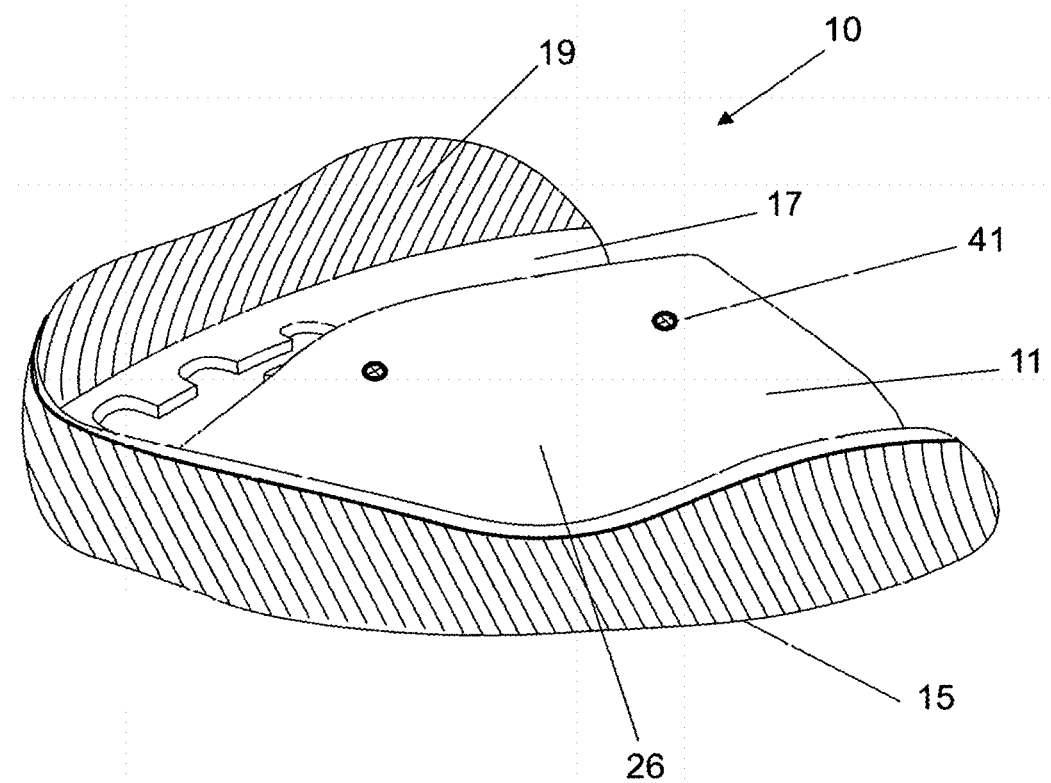
FIG. 1 is a perspective view of the first embodiment of surgical guide for upper jaw in accordance with present invention.

10 Surgical guide for dental implants for upper jaw
30 Surgical guide for dental implants for lower jaw
17 Base portion of surgical guide for upper jaw
18 Base portion of surgical guide for lower jaw
19 Arcuated buccal wall for upper surgical guide
23 Arcuated buccal wall for lower surgical guide
11 Top plate for upper surgical guide
12 Top plate for lower surgical guide
13 Bottom plate for upper surgical guide
14 Bottom plate for lower surgical guide
41 Connecting screw
15 Outer buccal edge of surgical guide for upper jaw
16 Outer buccal edge of surgical guide for lower jaw
24 Outer lingual edge of surgical guide for upper jaw
20 Outer lingual edge of surgical guide for lower jaw
21 Lingual wall of surgical guide for upper jaw
22 Lingual wall of surgical guide for lower jaw
25 Lingual upwardly extending arch concave surface of surgical guide for upper jaw
26 Palatal upwardly extending arch convex surface of surgical guide for upper jaw
59 Mounting navigated device
60 Guided tube
61 Plate
62 Rotatable head
63 Collar
64 Drill guided sleeve
65 Major perforated L track
66 Narrowed portion of the track
67 Supplemental short slots

DETAILED DESCRIPTION OF ILLUSTRATIVE EMBODIMENTS

An embodiment of set of surgical drill guides aimed at locating the ideal position for dental implants in edentulous patients for upper and lower jaws 10 and 30 respectively, of present invention, is shown in FIGS. 1-13.

Referring to FIG. 1, a surgical drill guide for upper jaw 10 is generally fan-shaped in plan. One embodiment 10 includes a base portion 17. The base is normally defined by an arcuated buccal wall 19 and this wall 19 extends mostly vertical from the base portion 17 and the created outer edge 15. The upper surgical guide comprises at least two plates: top plate 11 and bottom plate (not shown), which are connected together by means of screws 41. In addition, the present embodiment 10 is provided with a palatal upwardly convex extending arch surface 26.

Figure 2:
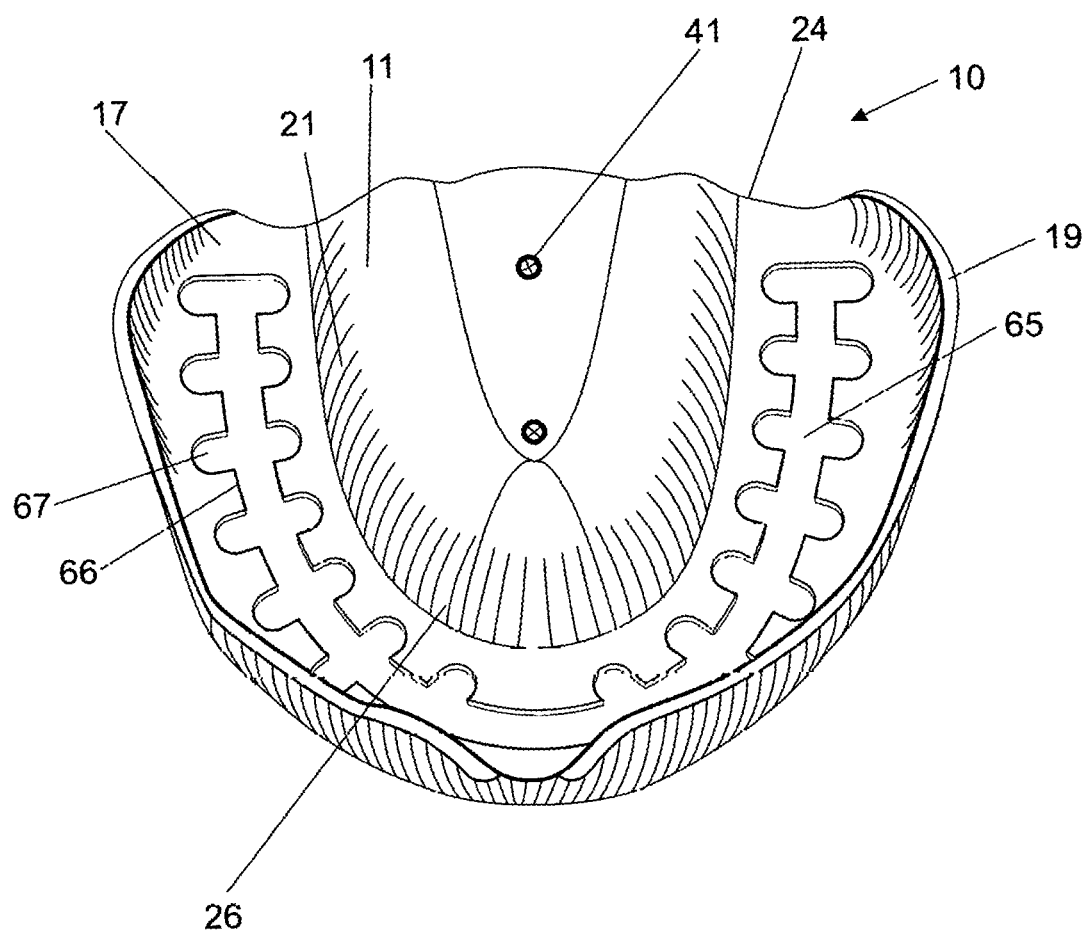
FIG. 2 is a top plan view of the tissue side of a surgical guide for upper jaw of FIG. 1.

Preferably, each surgical guide consists of at least 2 plates: top plate 11 and 12 respectively and bottom plate 13 and 14 respectively, which are connected together by means of screws 41 (see FIGS. 1-6);

As illustrated in FIG. 2 surgical drill guide for upper jaw 10 contains base portion 17 in which is located the major perforated L track 65, consisting of perforated portion and narrowed portion 66 and added by supplemental short slots 67. The base portion 17 is connected from mesial side to the top plate 11 and connected with bottom plate (not shown) by screws 41 which follow by the palatal upwardly convex extending arch surface 26 and the lingual wall 21 of surgical drill guide 10 and forms the outer lingual edge 24 and from the distal side base portion 17 defined by arcuated buccal wall 19.

Therefore, the surgical guide for upper jaw 10 is provided with spherical upwardly palatal ledge extension which covers the area between outer edges 15 and 23 of base portion 17 for better support and stability of surgical guide as illustrated in FIG. 2.

Figure 3:
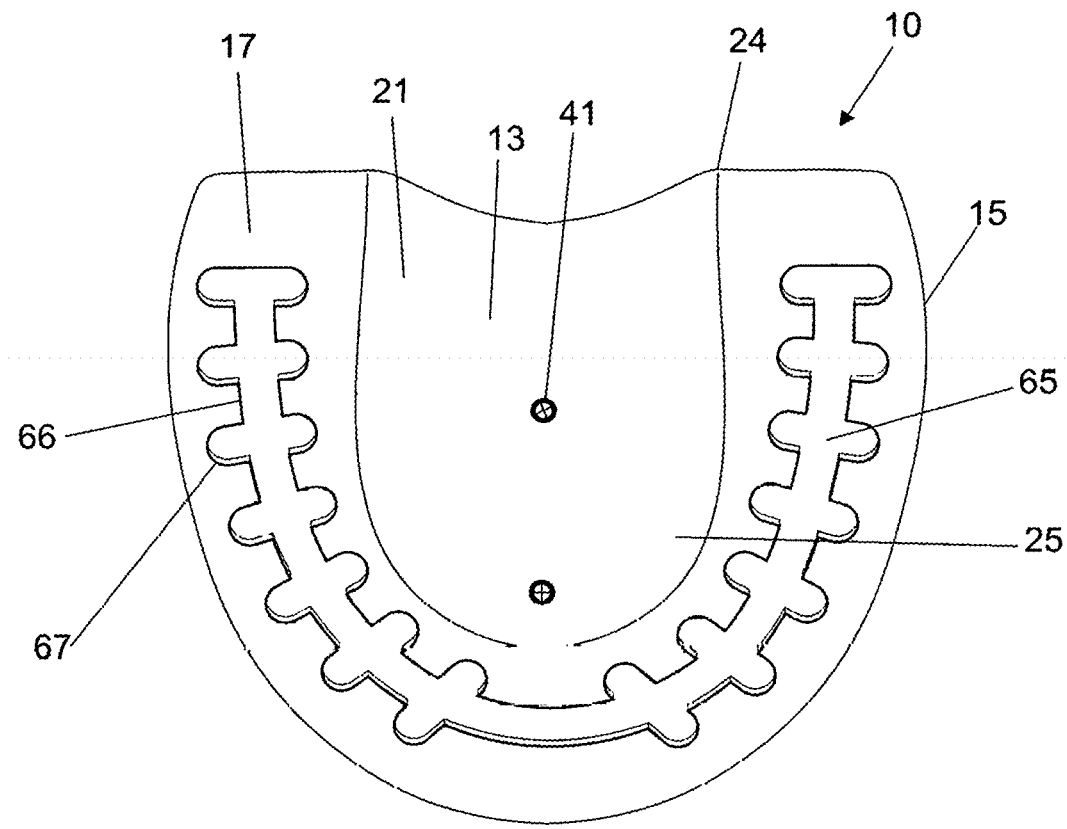
FIG. 3 is a bottom plan view of another embodiment in accordance with the present invention.

As seen in FIG. 3, the main member 10 comprises a bottom plate 13. The bottom plate lengthens and forms the lingual wall 21 and the outer lingual edge 24. The lingual outer edge extends from the base portion 17 in which the major perforated L track 65, consisting of a perforated portion and a narrowed portion 66, combined with supplemental short slots 67 that are located and which in turn ends by outer edge 15. The mesial to lingual edge is situated lingual upwardly extending arch concave surface 25. The bottom plate 13 is connected with the top plate (not shown) by screws 41.

As shown in FIGS. 1-3, the top 11 and bottom 13 plates of surgical guide for upper jaw 10 have a fan-shaped design.

Figure 4:
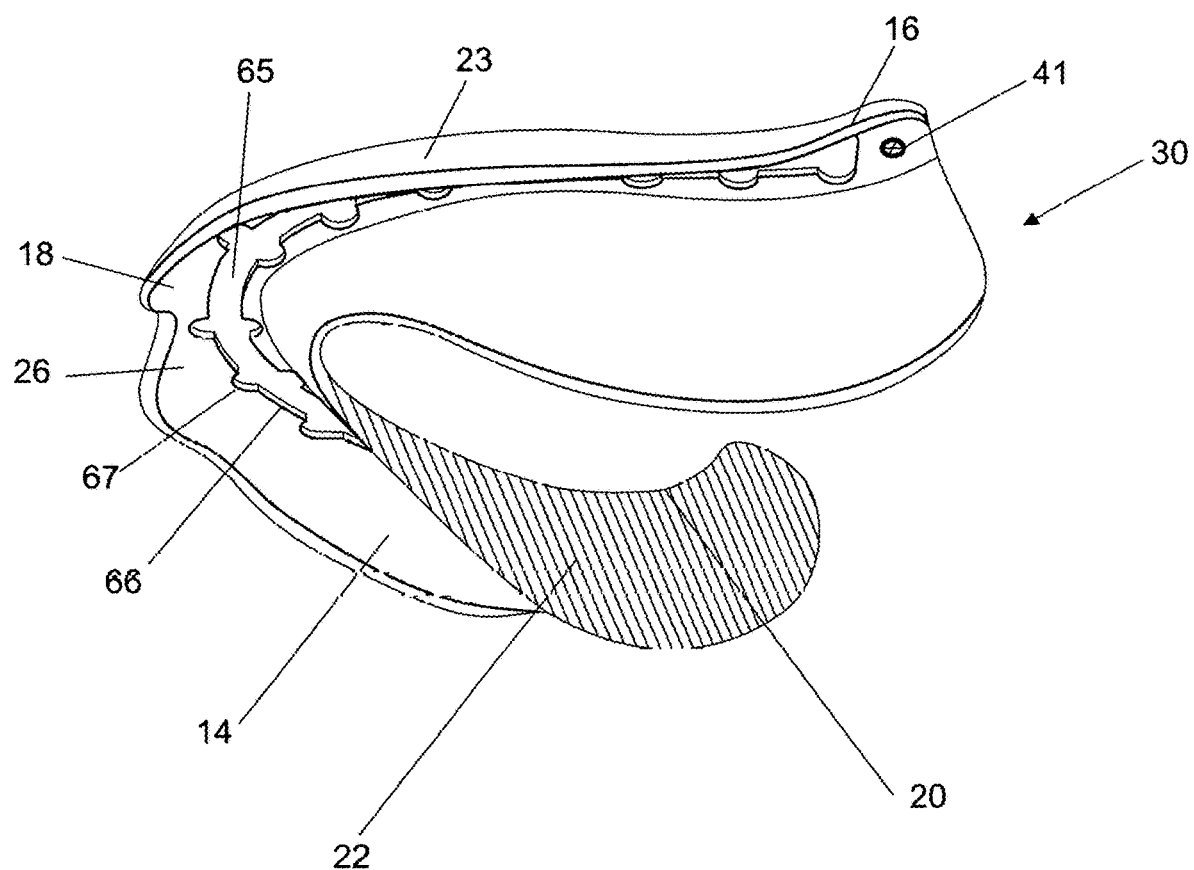
FIG. 4 is perspective view of the second embodiment of surgical guide for lower jaw in accordance with present invention.

Referring now to FIG. 4, a surgical drill guide for lower jaw 30 is mostly U shape in design. The one embodiment 30 comprises a base portion 18. The base is normally defined by an arcuated buccal wall 23 and this wall extends typically vertical from the base portion 18 and the outer edge 16. The surgical guide for lower jaw 30 comprises at least two plates: top plate (not shown) and bottom plate 14, which are connected together by means of screws 41. In addition, the present embodiment 30 is extended by the lingual wall 22 and the forming outer lingual edge 20. In addition, the present embodiment encloses the major perforated L track 65, containing the perforated portion, and the narrowed portion 66 in addition to the supplemental short slots 67.

An additional lingual wall 21 of lower surgical guide connects to the base portion of the lower surgical guide 18 and forms an internal angle 20 of approximately 90 degree.

Figure 5:
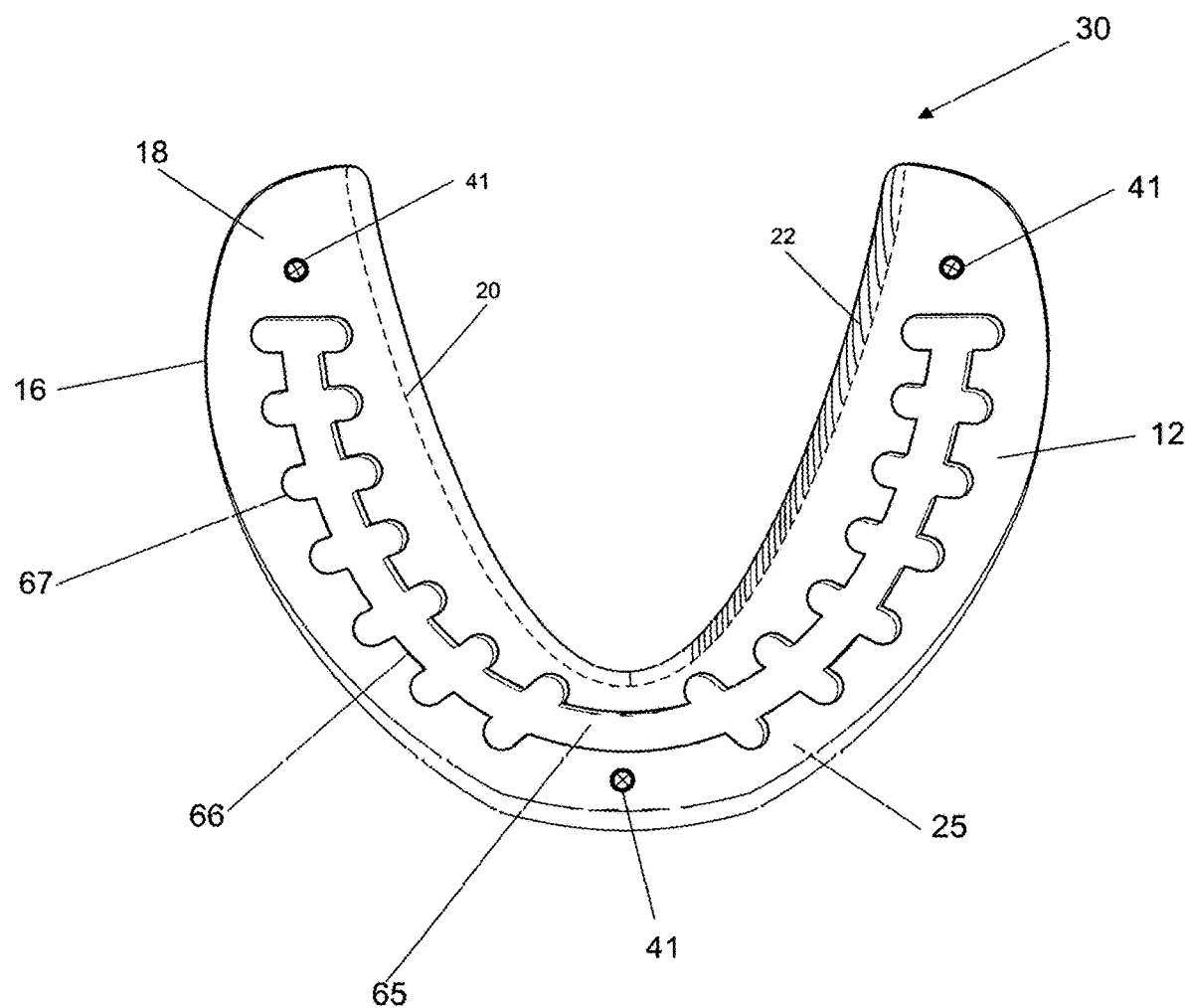
FIG. 5 is a top plan view of the second embodiment of surgical guide for lower jaw of FIG. 4.

As shown in FIG. 5 one embodiment 30 comprises by top plate 12. The top plate lengthens and developing lingual wall 22 and outer lingual edge 20. The lingual outer edge extends and creating base portion 18 in which the major perforated L track 65, consisting of a perforated portion and a narrowed portion 66 in addition to the supplemental short slots 67 that are located and which in turn ends by outer buccal edge 16. The top plate 12 is attached to the bottom plate 14 (not shown) by screws 41.

Figure 6:
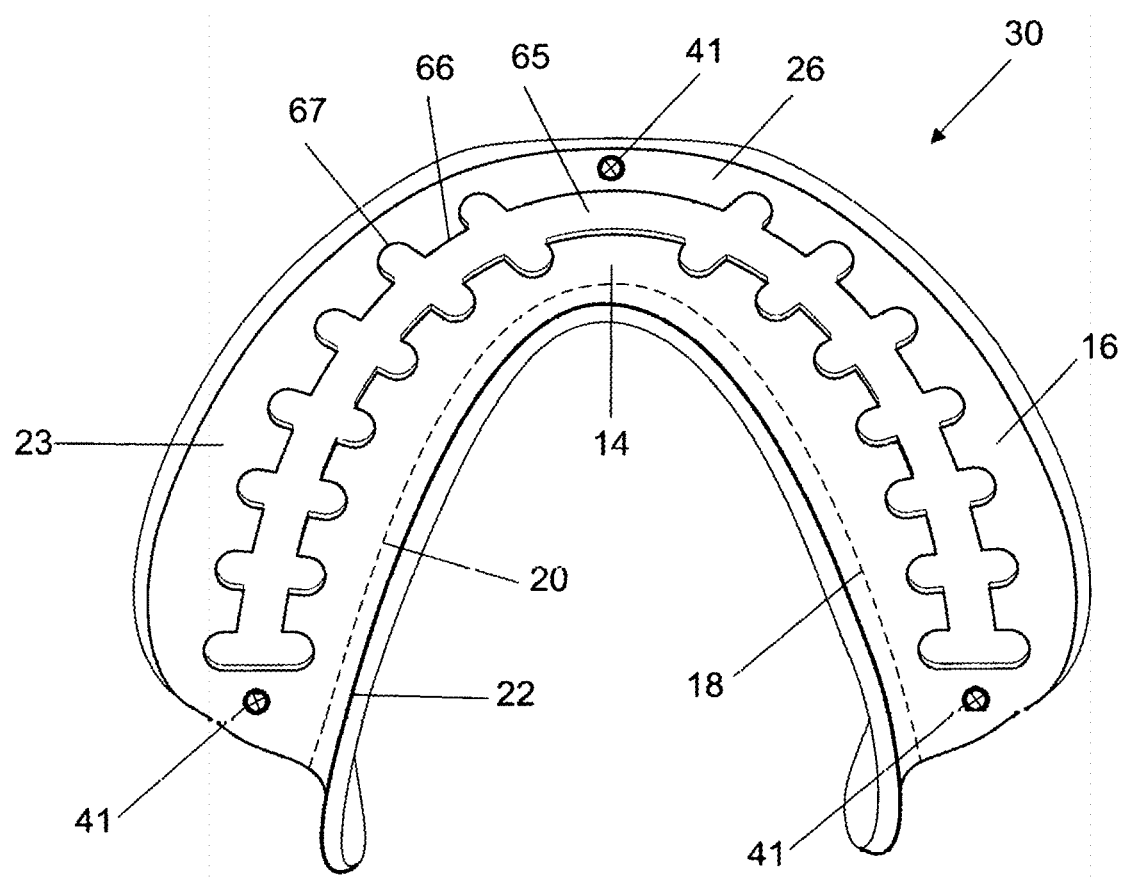
FIG. 6 is a bottom plan view of the tissue side of surgical guide for lower jaw of FIG. 4.

As demonstrated in FIG. 6 surgical drill guide for the lower jaw 30 contains a base portion 18 in which is located the major perforated L track 65, consisting of perforated portion and narrowed portion 66 in addition to supplemental short slots 67. The bottom plate 14 is connected to the top plate 16 (not shown) by screws 41. From distal side base portion 18 is defined by arcuated buccal wall 23. The base portion is extended by creating outer buccal edge 16. The bottom plate lengthens and developing lingual wall 22 and outer lingual edge 20.

As shown in FIGS. 1-6, the arcuated buccal walls 19 and 23 relatively connected to the bases portions of the surgical guides 17 and 18 correspondingly and form an angle of approximately 90 degrees.

With continue reference to FIGS. 1-6 it is desirable that each base 17 and 18 correspondingly is generally defined by the arcuated buccal edges 15 and 16 respectively and the arcuated lingual edges 17 and 20 accordingly.

As shown in FIGS. 4-6, preferably the top plate 12 and bottom plate 14 of surgical the surgical guide for upper and lower jaws correspond to the forms and contour of upper and lower jaws of the patient. Each surgical guide includes a base portion 17 and 18 respectively. Each base is defined by an arcuated front walls 19 and 23 respectively (see FIGS. 1-6).

Figure 7:
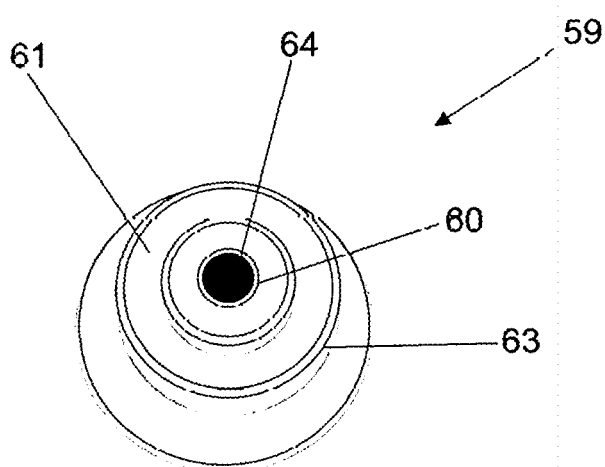
FIG. 7 is a bottom view of the mounting devise of the present invention.
Figure 8:
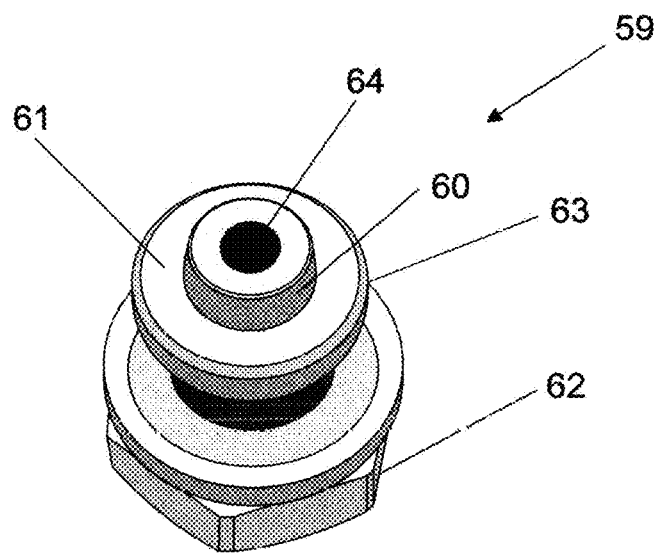
FIG. 8 is a bottom perspective view of the mounting devise of the present invention.
Figure 9:
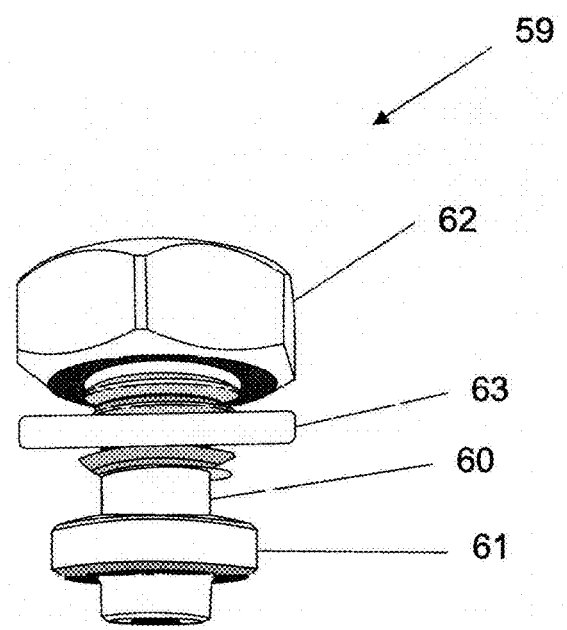
FIG. 9 is a perspective view of the embodiment of mounting devise for surgical guide for upper and lower jaw in accordance with present invention.

With continuing reference to FIGS. 7-9, another embodiment of the mounting navigated device 59 of present invention is shown. Mounting navigated device comprises a guided tube 60 and plate 61. The mounting navigated device extends from the rotatable head 62 in the top and may comprise collar 63 and drill guided sleeve 64 as seen in FIG. 7-9.

As illustrated in FIGS. 7, 8, 9, the mounting device 59 may be constructed from a rigid material such as metal or plastic and mounted and aligned to orientation marks according to position of natural teeth in the patient mouth.

The mounting navigated device extends from rotatable head 62 in the top and may comprise the collar 63 and the drill guided sleeve 64 (see FIGS. 7-9).

Figure 10:
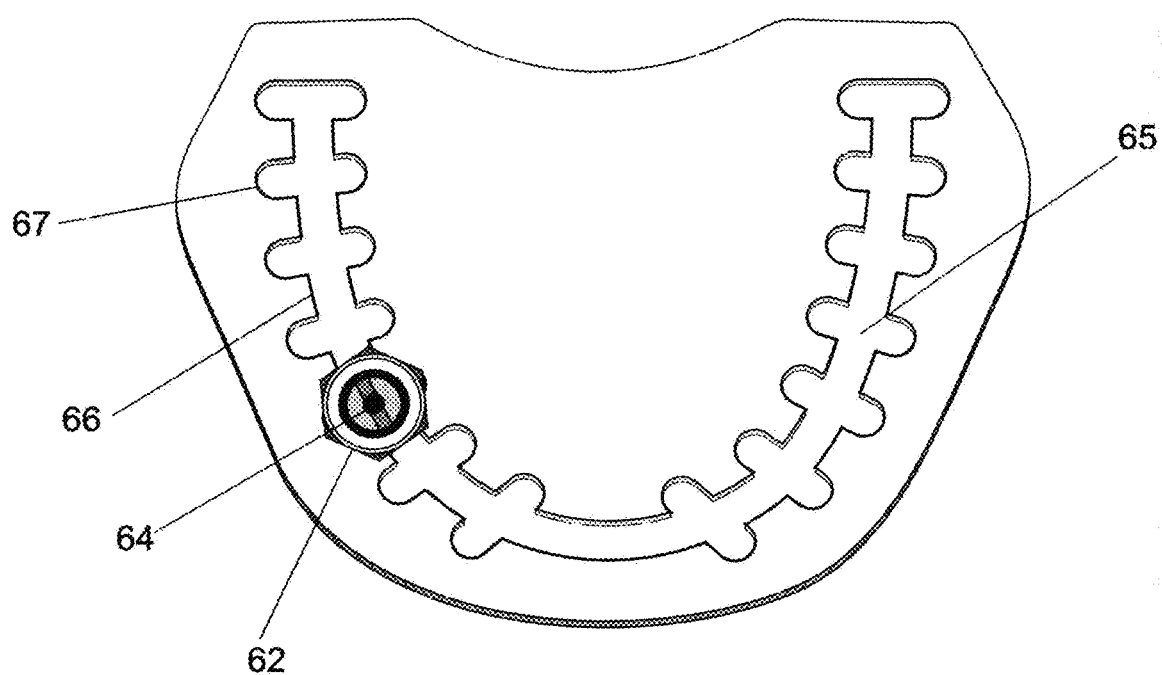
FIG. 10 is a top view of apparatus of FIG. 1 with the mounting device secured to the visible portion of perforated L track of present invention.

Referring to FIG. 10, one embodiment of a major perforated L track 65 fitting mounting navigated assembly includes but is not limited to a rotatable head 62 and drill guided sleeve 64. In this particular embodiment, the rotatable head is used to fix in the desired position the mounting navigated device for subsequent drilling with a drill through guided sleeve 64 and guided tube 60 (not shown). It is contemplated that the guided sleeve and the guided tube is 2 mm or more, although the sleeve and the tube can be varied depending on the implant system. In fact, because guided tube 60 is positioned above the top surface of L track, the narrowed portion 66 and the supplemental short slots 67, the diameter of plate 61 (not shown) is not limited by the width of the diameter of the track. The locking mechanism or plate 61 (not shown) is shaped to match the outlines of L-track.

Figure 11:
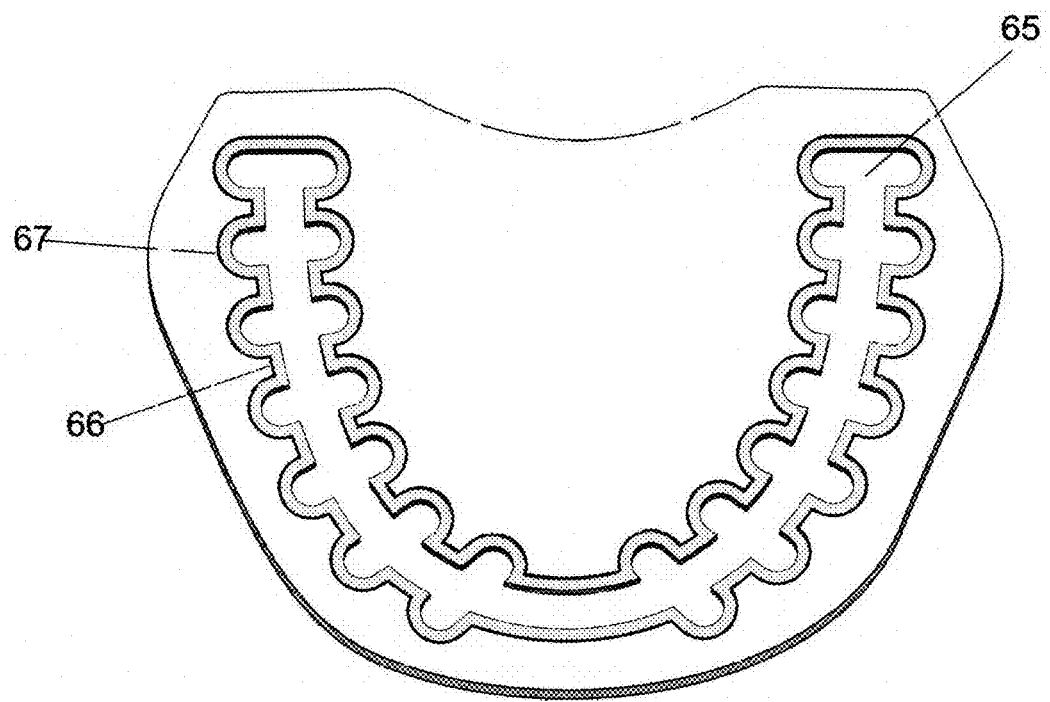
FIG. 11 is a top view of disassembled inner surface of present invention, showing the "hidden" contours of visible potion of L track.
Figure 12:
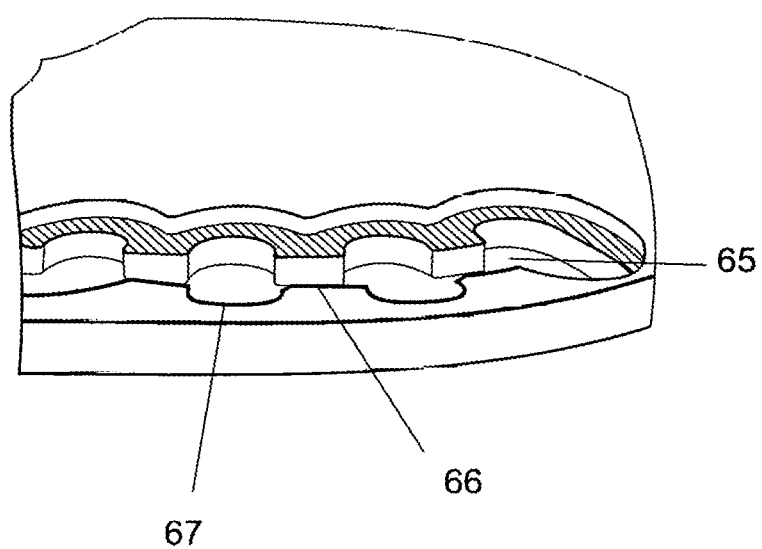
FIG. 12 is a perspective view of a portion of major perforated L track, for which one of the embodiments is fitted.
Figure 13:
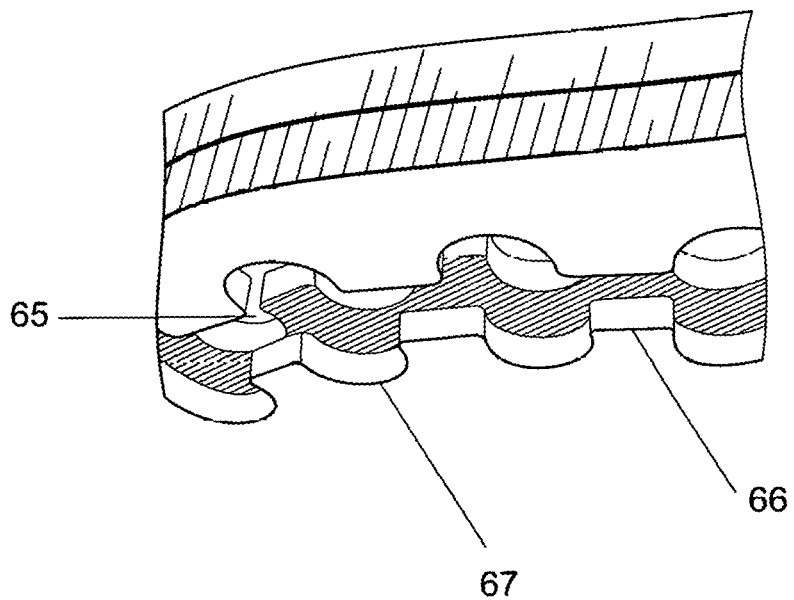
FIG. 13 is a bottom perspective view of a portion of major perforated L track and supplemental short slots.

With reference to FIGS. 11, 12, 13, the major perforated L track 65 is comprised of a plurality of supplemental short slots 67 which are interspersed with narrowed portions of track 66 corresponding to the natural position of absent teeth.

The internal profile outlines of FIGS. 11-13 show the contours of the main L track 65 space underneath, containing shapes of the supplemental short slots 67 and the narrowed portions of the track 66.

Figure 14:
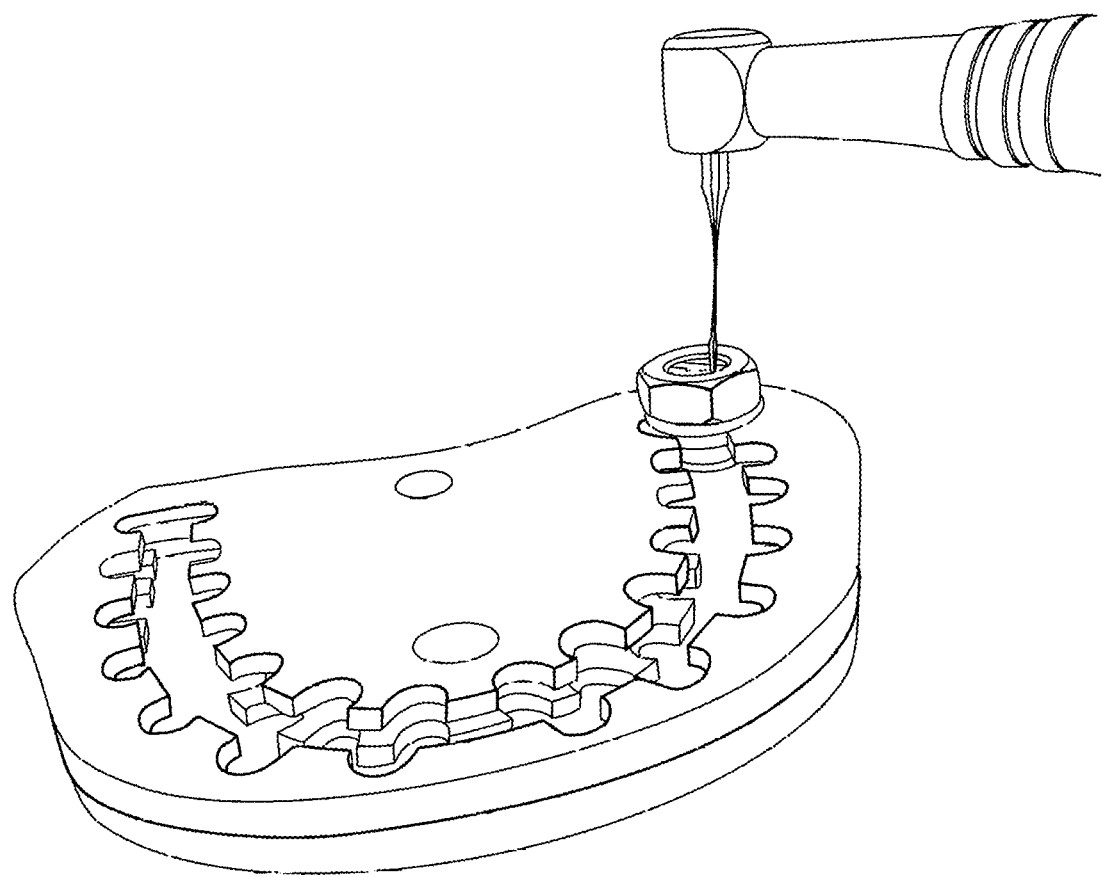
FIG. 14 illustrates a drill installing a mounting device of surgical guide.

FIG. 14 illustrates an example how the drill can be generally handled by a headpiece to be installed and inserted into a mounting device of surgical guide.

What is claimed is:

1. A surgical drill guide assembly comprising:
   a template configured to locate an ideal position for a dental implant in an edentulous patient, wherein said template comprises:
   a top plate;
   a bottom plate;
   said top plate further comprising a substantially U-shaped track comprising a plurality of cross hatched locations intersecting said U-shaped track corresponding to locations where an implant may be placed;
   said bottom plate further comprising a substantially U-shaped track comprising a plurality of cross hatched locations intersecting said U-shaped track corresponding to locations where an implant may be placed;
   wherein the top and bottom plates are connected by screws;
   wherein the top and bottom plates are configured to be fitted on and retained over soft tissue of a patient's mouth in a fully edentulous upper or lower jaw;
   wherein said U-shaped track of the top plate and said U-shaped track of said bottom plate together form a parallel set of U-shaped tracks; and
   a navigation device configured to be mounted within said template and move along said parallel set of U-shaped tracks to place implants in defined locations in the jaw.

2. The assembly of claim 1, wherein said template is comprised of metal material.

3. The assembly of claim 1, wherein said template is fan-shaped when configured to be placed in the upper jaw.

4. The assembly of claim 1, wherein said template is U-shaped when configured to be placed in the lower jaw.

5. The assembly of claim 1, wherein said navigation device further comprises:
   a guide tube extending downward from a top surface of a surgical guide, wherein the guide tube comprises:
   a navigating hole which receives drill bits for drilling, wherein the guide tube has a lip configured to be used as a locking tool to attach an osteotomy drill; and
   a driving element or rotatable head used as a fixation element configured to lock the navigation device at a desired position in a patient's mouth.

6. A method of inserting a dental implant in a mouth of an edentulous patient comprising:
   providing the assembly of claim 1;
   mounting the template over soft tissue of the edentulous patient;
   directing the navigation device along the template using the parallel set of U-shaped tracks;
   locking the navigation device in a desired position;
   drilling apertures for the insertion of the dental implant through a guide tube connected to the parallel set of U-shaped tracks; and
   after drilling the drilling apertures, removing the surgical guide from the mouth of the patient.

* * * * *